United States Patent
Türk et al.

(10) Patent No.: US 9,492,382 B2
(45) Date of Patent: Nov. 15, 2016

(54) HYPERBRANCHED POLYESTER HAVING A HYDROPHOBIC CORE FOR SOLUBILIZING ACTIVE INGREDIENTS OF LOW SOLUBILITY

(75) Inventors: Holger Türk, Mannheim (DE); Monika Haberecht, Ludwigshafen (DE); Hiroe Yamada, Saarbrücken (DE); Bernd Bruchmann, Freinsheim (DE); Daniel Schönfelder, Bruxelles (BE); Michael Ishaque, Mannheim (DE); Joachim Clauss, Darmstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/515,864

(22) PCT Filed: Dec. 15, 2010

(86) PCT No.: PCT/EP2010/069683
§ 371 (c)(1),
(2), (4) Date: Jul. 3, 2012

(87) PCT Pub. No.: WO2011/073222
PCT Pub. Date: Jun. 23, 2011

(65) Prior Publication Data
US 2012/0264609 A1 Oct. 18, 2012

(30) Foreign Application Priority Data

Dec. 18, 2009 (EP) .................................. 09179901
Apr. 21, 2010 (EP) .................................. 10160526

(51) Int. Cl.
| | | |
|---|---|---|
| A01P 21/00 | (2006.01) |
| A01P 7/04 | (2006.01) |
| A01P 3/00 | (2006.01) |
| C08G 63/91 | (2006.01) |
| A01N 25/10 | (2006.01) |
| A01P 13/00 | (2006.01) |
| A01P 5/00 | (2006.01) |
| A61K 9/06 | (2006.01) |
| A01N 25/02 | (2006.01) |
| A61K 47/34 | (2006.01) |
| C08G 18/28 | (2006.01) |
| C08G 83/00 | (2006.01) |
| C08G 18/62 | (2006.01) |
| C08G 18/80 | (2006.01) |
| C08G 18/42 | (2006.01) |

(52) U.S. Cl.
CPC .............. *A61K 9/06* (2013.01); *A01N 25/02* (2013.01); *A61K 47/34* (2013.01); *C08G 18/283* (2013.01); *C08G 18/4241* (2013.01); *C08G 18/4277* (2013.01); *C08G 18/622* (2013.01); *C08G 18/8016* (2013.01); *C08G 83/005* (2013.01)

(58) Field of Classification Search
None
See application file for complete search history.

(56) References Cited

U.S. PATENT DOCUMENTS

| 2006/0034889 A1* | 2/2006 | Jo ........................ A61K 9/0024 424/426 |
| 2007/0027269 A1 | 2/2007 | Stumbe et al. |
| 2007/0160561 A1* | 7/2007 | Ouali et al. ................ 424/70.16 |
| 2009/0099319 A1 | 4/2009 | Stumbe et al. |

FOREIGN PATENT DOCUMENTS

| WO | WO 96/07688 | 3/1996 |
| WO | WO 2005/037893 | 4/2005 |
| WO | WO 2007/125028 | 11/2007 |
| WO | WO 2007/125041 | 11/2007 |

OTHER PUBLICATIONS

Meerod et al., "Magnetite nanoparticles stabilized with polymeric bilayer of poly (ethylene glycol) methyl ether-poly(epsilon-caprolactone copolymers" Polymer, (Aug. 2008), vol. 49, Issue 18, pp. 3950-3956.*
International Search Report, PCT/EP2010/069683, filed Dec. 15, 2010.
International Preliminary Report on Patentability, PCT/EP2010/069683, filed Dec. 15, 2010.
Brenner et al., "Hyperbranched Polyesters: End Group Modification and Properties", Macromolecular Symposia, vol. 102, Jan. 1, 1996, pp. 47-54, XP000597880.

* cited by examiner

Primary Examiner — Abigail Fisher
Assistant Examiner — Daniel Branson
(74) Attorney, Agent, or Firm — Brinks Gilson & Lione

(57) ABSTRACT

The present invention provides a composition comprising an active ingredient with a maximum solubility in water at 20° C. of 10 g/l, and a hyperbranched polyester which is joined to a polar polymer which comprises a polycondensate or a polymer comprising ethylenically unsaturated monomers. The invention further relates to the hyperbranched polyester mentioned and to a process for preparation thereof. It further relates to the use of the hyperbranched polyester for solubilizing the active ingredient in aqueous compositions.

7 Claims, No Drawings

HYPERBRANCHED POLYESTER HAVING A HYDROPHOBIC CORE FOR SOLUBILIZING ACTIVE INGREDIENTS OF LOW SOLUBILITY

This application is a National Stage application of International Application No. PCT/EP2010/069683, filed Dec. 15, 2010, the entire contents of which is hereby incorporated herein by reference. This application also claims priority under 35 U.S.C. §119 to European Patent Application No. 09179901.5, filed Dec. 18, 2009, and to European Patent Application No. 10160526.9, filed Apr. 21, 2010, the entire contents of which are hereby incorporated herein by reference.

The present invention provides a composition comprising an active ingredient with a maximum solubility in water at 20° C. of 10 g/l, and a hyperbranched polyester which is joined to a polar polymer which comprises a polycondensate or a polymer comprising ethylenically unsaturated monomers. The invention further relates to the hyperbranched polyester mentioned and to a process for preparation thereof. It further relates to the use of the hyperbranched polyester for solubilizing the active ingredient in aqueous compositions. Combinations of preferred features with other preferred features are encompassed by the present invention.

In many cases it is necessary to solubilize hydrophobic active ingredients in water without chemically modifying the relevant active ingredient per se. For this purpose it is possible for example to prepare an emulsion in which the relevant active ingredient is in the oil phase of the emulsion. However, with many active pharmaceutical ingredients or especially crop protection compositions, especially in the case of those which are to be transported with a body fluid or in a plant's sap, an approach of this kind is not possible. Under the action of high shearing forces it is possible for emulsions to break. Moreover, sterilizing while retaining the emulsion is in many cases not a possibility.

Compositions comprising an active ingredient and a hyperbranched polyester are common knowledge:

WO 2007/125028 discloses a process for solubilizing hydrophobic active ingredients in an aqueous medium, wherein a hyperbranched polyester which has optionally been reacted with a polyalkylene oxide unit which bears an isocyanate group is used. To prepare the polyester, a wide variety of different dicarboxylic acids are described, such as sebacic acid, and a wide variety of different trifunctional alcohols, such as glycerol, trimethylolpropane, pentaerythritol and alkoxylated derivatives thereof. The polyester can be reacted with a reaction product of diisocyanate having a capped polyalkylene glycol.

Hyperbranched polyesters are common knowledge:

WO 2009/047210 discloses hyperbranched polyesters comprising dicarboxylic acid units and trifunctional alcohols, the dicarboxylic acid units described being succinic acid units substituted by $C_3$-$C_{40}$ alkyl radicals or alkenyl radicals. A wide variety of different trifunctional alcohols are mentioned, such as glycerol, trimethylolpropane, pentaerythritol and alkoxylated derivatives thereof.

WO 2007/068632 discloses hyperbranched polyesters obtainable by reacting dicarboxylic acids having polyisobutene groups and trifunctional alcohols such as glycerol, trimethylolpropane, pentaerythritol and the alkoxylated derivatives thereof. The polyester can subsequently be functionalized.

A disadvantage of the known hyperbranched polyesters is that they can solubilize only small amounts of sparingly soluble active ingredients since they do not usually possess a markedly amphiphilic structure. Moreover, the polyesters are often themselves not water-soluble or not water-dispersible, such that they are unsuitable for solubilization in aqueous media. Even a neutralization of the carboxylic acid groups present could not achieve water solubility, since the acid number is usually very low, for example less than 50 or even less than 20 mg KOH per g of polymer.

It was an object of the present invention to find an alternative hyperbranched polyester which is suitable for solubilizing sparingly soluble active ingredients, in particular in an aqueous medium. It was a further object to find a polyester which can solubilize maximum amounts of active ingredient, especially active agrochemical ingredient, and which should have maximum stability, especially hydrolytic stability. In addition, the polyester should itself be water-soluble or water-dispersible, either by virtue of functionalization by means of a polyalkylene oxide group and/or of a functional $C_1$-$C_{24}$ end group comprising one acid group or two alcohol groups, and/or by virtue of the existence of numerous, optionally (partly) neutralizable carboxylic acid groups. Finally, it was also an object of the invention to find a hyperbranched polyester which is preparable readily from commercially available chemicals and in an industrially reliable manner.

The object was achieved by a composition comprising an active ingredient with a maximum solubility in water at 20° C. of 10 g/l, and a hyperbranched polyester which is joined to a polar polymer which comprises a polycondensate or a polymer comprising ethylenically unsaturated monomers.

The maximum solubility of the active ingredient in water at 20° C. is 10 g/l, preferably 2 g/l, more preferably 0.5 g/l and especially 0.1 g/l. The composition may comprise one or more different active ingredients. Examples of active ingredients are active agrochemical ingredients, active cosmetic ingredients, active pharmaceutical ingredients or food supplements (such as vitamins or carotenoids). Preferred active ingredients are active agrochemical ingredients.

Examples of active cosmetic ingredients are cosmetic oils, flavorings and aromas, vitamins or UV absorbers. Cosmetic oils include groundnut oil, jojoba oil, coconut oil, almond oil, olive oil, palm oil, castor oil, soybean oil, wheatgerm oil, or essential oils such as mountain pine oil, lavender oil, rosemary oil, spruce needle oil, pine needle oil, eucalyptus oil, peppermint oil, sage oil, bergamot oil, terpentine oil, melissa oil, juniper oil, lemon oil, anise oil, cardamom oil, camphor oil, etc., or mixtures thereof. UV absorbers include 2-hydroxy-4-methoxybenzophenone, 2,2', 4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate and 2-isoamyl p-methoxycinnamate, and mixtures thereof.

Examples of flavorings and aromas are as described in WO 01/49817, or in "Flavors and Fragrances", Ullmann's Encyclopedia of Industrial Chemistry, Wiley-VCH, 2002, to which explicit reference is made.

Examples of vitamins are vitamins, provitamins and vitamin precursors from groups A, C, E and F, especially 3,4-didehydroretinol, beta-carotene (provitamin of vitamin A), ascorbic acid (vitamin C), and the palmitic esters, glucosides or phosphates of ascorbic acid, tocopherols, especially alpha-tocopherol and esters thereof, for example the acetate, the nicotinate, the phosphate and the succinate;

and additionally vitamin F, which is understood to mean essential fatty acids, particularly linolic acid, linolenic acid and arachidonic acid.

Examples of active pharmaceutical ingredients include: benzodiazepines, antihypertensives, vitamins, cytostatics, especially taxol, anesthetics, neuroleptics, antidepressives, antiviral agents, for example anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutics, psychoactive drugs, Parkinson's drugs and other antihyperkinetics, ophthalmics, neuropathy preparations, calcium metabolism regulators, muscle relaxants, lipid-lowering drugs, hepatotherapeutics, coronary drugs, cardiac drugs, immunotherapeutics, regulatory peptides and inhibitors thereof, hypnotics, sedatives, gynecologicals, gout remedies, fibrinolytics, enzyme preparations and transport proteins, enzyme inhibitors, emetics, blood flow stimulators, diuretics, diagnostic agents, corticoids, cholinergics, biliary therapeutics, antiasthmatics, bronchodilators, beta receptor blockers, calcium antagonists, ACE inhibitors, arteriosclerosis drugs, antiinflammatories, anticoagulants, antihypotensives, antihypoglycaemics, antihypertensives, antifibrinolytics, antiepileptics, antiemetics, antidotes, antidiabetics, antiarrhythmics, antianaemics, antiallergics, anthelmintics, analgesics, analeptics, aldosterone antagonists, slimming agents.

The term "active agrochemical ingredients" (also referred to hereinafter as pesticides) refers to at least one active ingredient selected from the group of fungicides, insecticides, nematicides, herbicides, safeners and/or growth regulators. Preferred pesticides are fungicides, insecticides and herbicides, especially insecticides. Mixtures of pesticides from two or more of the abovementioned classes can also be used. The person skilled in the art is familiar with such pesticides, which can be found, for example, in Pesticide Manual, 14th Ed. (2006), The British Crop Protection Council, London. Suitable insecticides are insecticides from the class of carbamates, organophosphates, organochlorine insecticides, phenylpyrazoles, pyrethroids, neonicotinoids, spinosins, ivermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof. Suitable fungicides are fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino) pyrimidines, hydroxyanilides, imidazoles, imidazolinones, inorganic compounds, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides of the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment, the pesticide comprises an insecticide; the pesticide more preferably consists of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenozide and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Very particularly preferred insecticides are fipronil, alpha-cypermethrin, deltamethrin, chlorfenapyr, hydramethylnon and metaflumizone. An especially preferred insecticide is fipronil. In a further embodiment, the pesticide comprises a fungicide; the pesticide preferably consists of at least one fungicide. Preferred fungicides are pyraclostrobin, metconazol and epoxiconazol. In a further embodiment, the pesticide comprises a herbicide; the pesticide preferably consists of at least one herbicide. In a further embodiment, the pesticide comprises a growth regulator; the pesticide preferably consists of at least one growth regulator.

The inventive composition comprises typically 0.1 to 70% by weight of active ingredient, preferably 1 to 60% by weight, especially 3 to 50% by weight, based on the composition. The inventive composition usually comprises 0.01 to 40% by weight, preferably 0.05 to 30% by weight, more preferably 0.1 to 20% by weight, of hyperbranched polyester. The weight ratio of the hyperbranched polyester to the active ingredient is usually in the range from 1:2 to 25:1.

Dendrimeric and hyperbranched polymers are terms for polymers which are notable for a highly branched structure and a high functionality. However, there are nevertheless significant differences in structure between dendrimers and hyperbranched polymers. Dendrimers are molecularly homogeneous macromolecules with a highly symmetric structure. Dendrimers can, proceeding from a central molecule, be prepared by controlled stepwise linkage of in each case two or more di- or polyfunctional monomers to each already bonded monomer. Each linkage step multiplies the number of monomer end groups (and hence of linkages) by the factor of 2 or higher, and monodisperse polymers which are built up generation by generation and have treelike structures, ideally spherical, whose branches each comprise exactly the same number of monomer units, are obtained. Owing to the branched structure, the polymer properties are advantageous: for example, a surprisingly low viscosity and a high reactivity are observed owing to the high number of functional groups on the sphere surface. However, the preparation of the monodisperse dendrimers is complicated by the need to introduce protecting groups and remove them again in each linkage step, and by the requirement for intensive purifying operations before the start of each new growth stage, which is why dendrimers are typically prepared only on the laboratory scale.

In contrast, hyperbranched polymers are both molecularly and structurally inhomogeneous, i.e. the molecules of the polymer have a distribution both with regard to the molecular weight and with regard to the structure of the molecules. They are obtained by being built up in a non-generational manner. It is therefore also not necessary to isolate and to purify intermediates. Hyperbranched polymers can be obtained by simple mixing of the components required to form them and the reaction thereof in a so-called one-pot reaction. Hyperbranched polymers may have dendrimeric substructures. In addition, though, they also have linear polymer chains and inhomogeneous polymer branches.

Especially suitable for the synthesis of hyperbranched polymers are so-called $AB_x$ monomers. These have two different functional groups A and B in one molecule, which can react with one another in an intermolecular manner to form a bond. The functional A group is present only once per molecule and the functional B group twice or more than twice. The reaction of said $AB_x$ monomers with one another forms uncrosslinked polymers with a high number of branching sites. The polymers have almost exclusively B groups at the chain ends.

Moreover, hyperbranched polymers can be prepared via the $A_x+B_y$ synthesis route. In this case, $A_x$ and $B_y$ represent two different monomers with the functional groups A and B, and the indices x and y the number of functional groups per monomer. In the $A_x+B_y$ synthesis, illustrated here by the example of an $A_2+B_3$ synthesis, a difunctional monomer $A_2$ is reacted with a trifunctional monomer $B_3$. This initially forms a 1:1 adduct of A and B with an average of one functional A group and two functional B groups, which can then likewise react to give a hyperbranched polymer. The hyperbranched polymers thus obtained also have predominantly B groups as end groups.

The nondendrimeric hyperbranched polymers used in accordance with the invention differ from dendrimers significantly in the degree of branching. The degree of branching DB of the polymers in question is defined as DB=100*(T+Z)/(T+Z+L), where T is the mean number of terminally bound monomer units, Z is the mean number of monomer units forming branches and L is the mean number of linearly bound monomer units in the macromolecules of the particular polymers. For the definition of the "Degree of Branching", see also H. Frey et al., Acta Polym. 1997, 48, 30. In the context of the invention, the feature "hyperbranched" in connection with the polymers means that the degree of branching DB is from 10 to 95%, preferably 25 to 90% and more preferably from 30 to 80%. A dendrimer, in contrast, has the maximum possible number of branching sites, which can be achieved only by a highly symmetric structure. In connection with the present invention, the polymers are "dendrimers", in contrast, when their degree of branching DB=99 to 100%.

In a known manner, the polyesters have ester linkages. The polymers comprise, as structural units, in each case at least one hydrophobic dicarboxylic acid unit and at least one trifunctional alcohol. They may additionally comprise further structural units. The hyperbranched polyester is usually soluble or dispersible in water, which means that it is possible to prepare a clear (i.e. without particles discernible to the naked eye) aqueous solution or dispersion.

The polyester is preferably based on a hydrophobic dicarboxylic acid which is an aliphatic $C_{10}$-$C_{32}$ dicarboxylic acid, a dicarboxylic acid having a polyisobutylene group and/or a succinic acid unit having a $C_3$-$C_{40}$ group. In a preferred embodiment, the hydrophobic dicarboxylic acid is an aliphatic $C_{10}$-$C_{32}$ dicarboxylic acid. In a further preferred embodiment, the hydrophobic dicarboxylic acid is a dicarboxylic acid having a polyisobutylene group. In a further preferred embodiment, the hydrophobic dicarboxylic acid is a succinic acid unit having a $C_3$-$C_{40}$ group. In a further preferred embodiment, the hydrophobic dicarboxylic acid is a dicarboxylic acid having a polyisobutylene group and/or a succinic acid unit having a $C_3$-$C_{40}$ group.

A suitable hydrophobic dicarboxylic acid is an aliphatic $C_{10}$-$C_{32}$ dicarboxylic acid. Preference is given to sebacic acid, α,ω-undecanedicarboxylic acid, α,ω-dodecanedicarboxylic acid, tridecanedicarboxylic acid (brassylic acid), especially sebacic acid.

Another suitable hydrophobic dicarboxylic acid is a dicarboxylic acid having a polyisobutylene group (also referred to hereinafter as "PIB diacid"). In this connection, a "dicarboxylic acid having a polyisobutylene group" has at least two dicarboxylic acid groups, at least two dicarboxylic ester groups or at least one dicarboxylic anhydride group (it preferably has one dicarboxylic anhydride group). Such PIB diacids are obtainable by reacting polyisobutylene with an enophile. In a preferred embodiment, the products are 1:1 (mol/mol) reaction products of an ene reaction of a polyisobutylene and of the enophile. The PIB diacid is prepared by the processes known to those skilled in the art and preferably as described in German laid-open specifications DE-A 195 19 042, preferably from page 2 line 39 to page 4 line 2 and more preferably from page 3 line 35 to 58, and DE-A 43 19 671, preferably from page 2 line 30 to line 68, and DE-A 43 19 672, preferably from page 2 line 44 to page 3 line 19, described processes for reacting polyisobutylenes with enophiles. The polyisobutylenes are preferably those which have to an extent of at least 60 mol % end groups formed from vinyl isomer and/or vinylidene isomer.

Suitable enophiles are fumaryl chloride, fumaric acid, itaconic acid, itaconyl chloride, maleyl chloride, maleic anhydride and/or maleic acid, preferably maleic anhydride or maleyl chloride, more preferably with maleic anhydride.

The number-average molecular weight $M_n$ of the PIB acid is preferably at least 100 g/mol, more preferably at least 200 g/mol. In general, the number-average molar mass $M_n$ is up to 5000, more preferably up to 2000 g/mol. In a particularly preferred embodiment, the PIB acids have a number-average molecular weight $M_n$ of 1000+/−500 g/mol.

The PIB diacid preferably has a structure of the general formula (Ia), (Ib) or (Ic), in which PIB may be a polyisobutylenyl group which is obtained by any polymerization and has a number-average molecular weight $M_n$ of 100 to 100 000 daltons. Preference is given to formula (Ia), i.e. PIB-succinic anhydride.

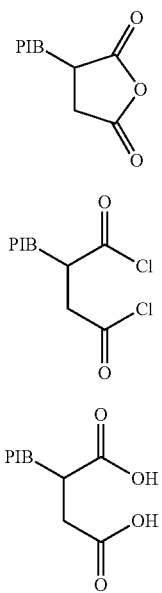

(Ia)

(Ib)

(Ic)

The number-average molecular weight $M_n$ of the thus obtainable and preferred succinic anhydride derivative substituted by a polyisobutylenyl group, known as "PIBSA", can be characterized by means of the hydrolysis number according to DIN 53401 in the unit mg KOH/g of substance. The synthesis of PIBSA is known in the literature as the ene reaction between maleic anhydride and polyisobutenes (see, for example, DE-A 43 19 672, EP-A 156 310).

During the ene reaction, a new α-olefin group is obtained at the chain end and is in turn again reactive. It is known to those skilled in the art that a reaction with further maleic anhydride affords a product which can thus bear two succinic anhydride groups per reactive chain end of the polyisobutene. This means that a polyisobutene from $BF_3$ catalysis, depending on the performance of the ene reaction, may bear one or even two succinic anhydride groups per chain. Consequently, polyisobutenes from living cationic polymerization in the reaction with maleic anhydride may likewise be mono- or disubstituted per reactive chain end. Thus, polyisobutenes are possible not just with one, but also with two and more succinic anhydride groups per molecule.

Since the reaction with maleic anhydride forms a new double bond which can likewise react with maleic anhydride, the succinic anhydrides which are substituted by a polyisobutylene group and are thus obtainable generally have a ratio of 0.9 to 1.5, preferably of 0.9 to 1.1, succinic anhydride groups per polyisobutylene chain. More preferably, each polyisobutylene chain bears only one succinic anhydride group.

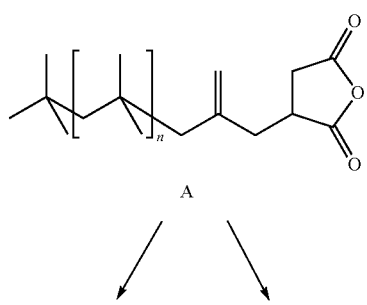

A

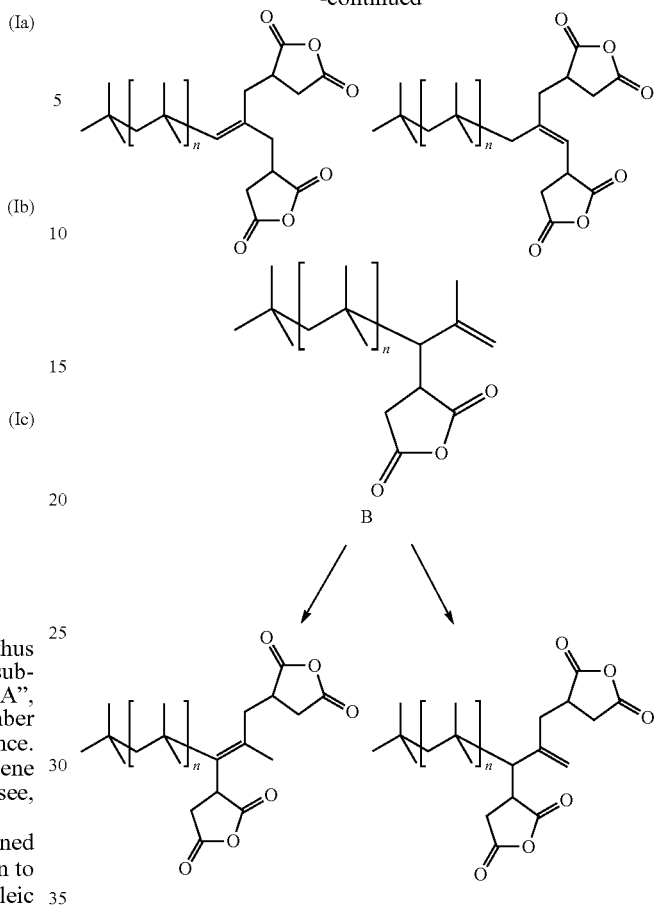

B

Shown above is an exemplary illustration of the product isomers of the single ene reaction and double ene reaction of an ideal polyisobutene having a single reactive chain end. Isomers are shown with one (alpha-olefin PIBSA, "A"; beta-olefin PIBSA, "B") or two succinic anhydride group(s) on one chain end. Analogously, however, PIBSAs having two and more chain ends are accordingly possible with one or two succinic anhydride radicals per chain end in the different isomeric variants of mono- and disubstitution. The number of possible isomers thus rises sharply with the number of chain ends. The person skilled in the art knows that, depending on the reaction, different substitution patterns can be realized with different isomer contents of the PIBSA.

The degree of functionalization, i.e. the fraction of the α- or β-olefinic end groups reacted with the enophile in the polyisobutene, of the polyisobutylene derivatives modified with terminal succinic anhydride groups is in total at least 65 mol %, preferably at least 75 mol % and most preferably at least 85 mol %. In the case of the polymers with only one reactive chain end, the degree of functionalization relates only to this one functional group with the two possible isomers α- and β-olefin PIBSA. In the disubstituted and polysubstituted PIBSA derivatives, the data for the degrees of functionalization are based on the total number of all functional groups within one molecule chain. Depending on whether mono- or disubstitution is present at one chain end, isomers depicted above are present in varying fractions.

The nonfunctionalized chain ends may either be those which have no reactive group at all (i.e. no α- or β-olefin radical) or those which do have a reactive group (α- or β-olefin radical) but which have not been reacted with maleic anhydride in the course of the ene reaction. In summary, the degree of functionalization thus relates only to the number of all functional groups present in one polymer chain, but not their possible isomers.

In addition, the copolymerization of maleic anhydride and polyisobutenes is also described, for example in WO 90/03359, EP B1 644 208, EP B1 744 413. The products thus prepared are known under the name polyPIBSA. In comparison to the ene reaction, however, copolymerization plays a comparatively minor role. This copolymerization of maleic anhydride and polyisobutenes, using free-radical initiators, forms alternating copolymers with comb structure. No homopolymers are known either of maleic anhydride or of polyisobutenes with olefinic end groups. It can thus be assumed that polyPIBSAs have a strictly alternating structure. A degree of functionalization as for the PIBSAs with terminal succinic anhydride units from the ene reaction cannot be specified. The structure of polyPIBSAs is depicted below.

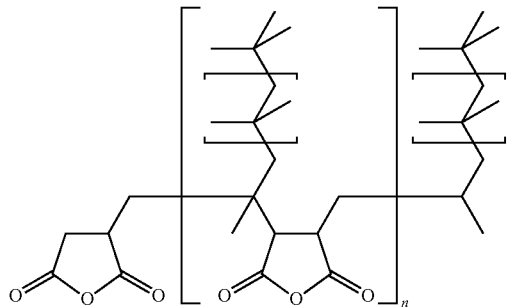

Suitable hydrophobic dicarboxylic acids are also succinic acid units having $C_3$-$C_{40}$ groups, preferably substituted succinic acid units of the formula (II)

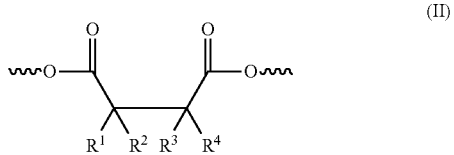

(II)

where $R^1$, $R^2$, $R^3$ and $R^4$ are each independently H, a $C_3$ to $C_{40}$-alkyl radical or a $C_3$ to $C_{40}$-alkenyl radical, with the proviso that at least one of the $R^1$, $R^2$, $R^3$ and $R^4$ radicals is not H. The radicals are preferably alkenyl radicals. Preferably two or three of the $R^1$, $R^2$, $R^3$ or $R^4$ radicals are H, and more preferably three of the radicals are H, i.e. the succinic acid unit has only one alkyl or alkenyl group. The one substituent may be in the $R^1$ or $R^3$ position.

The alkyl radicals may be linear or branched. They are preferably $C_4$ to $C_{30}$ radicals, more preferably $C_6$ to $C_{28}$ radicals, even more preferably $C_8$ to $C_{26}$ radicals and, for example, $C_{10}$ to $C_{20}$ radicals. The alkyl chains are more preferably linear. For example, they may be butyl, pentyl, hexyl, heptyl, octyl, decyl, dodecyl, tetradecyl, hexadecyl, octadecyl or isooctadecyl radicals, preferably decyl, dodecyl, tetradecyl, hexadecyl, octadecyl or isooctadecyl radicals. If the radicals are branched, preferably not more than one branch per 3 carbon atoms of the radical should be present, more preferably not more than one branch per 4 carbon atoms of the radical.

Alkenyl radicals have one or else more than one double bond. They are preferably alkenyl radicals with one double bond. The alkenyl radicals may be linear or branched. If the radicals are branched, preferably not more than one branch should be present per 3 carbon atoms of the radical, preferably not more than one branch per 4 carbon atoms of the radicals. They are preferably $C_4$ to $C_{30}$ radicals, more preferably $C_6$ to $C_{28}$ radicals, even more preferably $C_8$ to $C_{26}$ radicals and, for example, $C_{10}$ to $C_{20}$ radicals. The alkenyl radicals may preferably be n- or isohexenyl, n- or isoheptenyl, n- or isooctenyl, n- or isooctadienyl, n- or isononenyl, n- or isodecenyl, n- or isododecenyl, n- or isotetradecenyl, n- or isohexadecenyl, n- or isooctadecenyl or tetrapropenyl radicals. The alkenyl radicals are more preferably n- or isooctenyl, n- or isododecenyl, n- or isotetradecenyl, n- or isohexadecenyl, n- or isooctadecenyl or tetrapropenyl radicals.

To synthesize the hyperbranched polyesters, it is possible to use succinic acid substituted in the manner described. The succinic acid may preferably be used, however, in the form of activated derivatives, especially in the form of halides, esters or anhydrides.

Derivatives are especially the relevant anhydrides in monomeric or else polymeric form, mono- or dialkyl esters, preferably mono- or di-$C_1$-$C_4$-alkyl esters, more preferably mono- or dimethyl esters or the corresponding mono- or diethyl esters, and also mono- and divinyl esters and mixed esters, preferably mixed esters with different $C_1$-$C_4$-alkyl components, more preferably mixed methyl ethyl esters.

Particular preference is given to using succinic anhydrides as the starting material. In addition to the high reactivity of the anhydrides, the use of the anhydrides has the advantage that alkenylsuccinic anhydrides can be prepared in a particularly simple and inexpensive manner by reacting maleic anhydrides with olefins which have a hydrogen atom in the allyl position (the so-called ene reaction). Reaction of linear α-olefins can provide alkenylsuccinic anhydrides with n-alkenyl radicals; isomerized olefins with nonterminal double bonds give rise to succinic anhydrides substituted by isoalkenyl radicals. The olefins used may also be reactive oligo- or polyolefins, though reactive polyisobutenes are preferably not used. The preparation of alkenylsuccinic anhydrides (also known as ASA) by means of the ene reaction is described in detail, for example, in WO 97/23474 or DE 195 19 042 and the literature cited therein.

Succinic anhydrides substituted by alkenyl groups which are used with preference are n- or isohexenylsuccinic anhydride, n- or isoheptenylsuccinic anhydride, n- or isooctenylsuccinic anhydride, n- or isooctadienylsuccinic anhydride, n- or isononenylsuccinic anhydride, n- or isodecenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride, 2-dodecenyl-3-tetradecenylsuccinic anhydride. It will be appreciated that it is also possible to use mixtures of different substituted anhydrides.

Particularly preferred products are n- or isooctenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride or mixtures of the products mentioned. Very particular preference is given to n- or isohexadecenylsuccinic anhydride, n- or isooctadecenylsuccinic anhydride, or mixtures thereof.

The alkenylsuccinic acids or derivatives or mixtures thereof can also be used in a mixture with alkylsuccinic acids or derivatives thereof.

To prepare the hyperbranched polyesters, at least one hydrophobic dicarboxylic acid is reacted with at least one trifunctional alcohol, the ratio of the reactive groups in the reaction mixture being selected such that a molar ratio of OH groups to carboxyl groups or derivatives thereof of 5:1 to 1:5, preferably of 4:1 to 1:4, more preferably of 3:1 to 1:3 and most preferably of 2:1 to 1:2 is established. When mixtures of hydrophobic aliphatic $C_{10}$-$C_{32}$ dicarboxylic acids and/or dicarboxylic acids having polyisobutylene groups and/or succinic acid units having a $C_3$-$C_{40}$ group are used, the stoichiometry of OH groups to carboxyl groups is usually maintained as described above.

Trifunctional alcohols are understood to mean alcohols with at least three alcohol groups. Suitable trifunctional alcohols are glycerol, trimethylolethane, trimethylolpropane, bis(trimethylolpropane), pentaerythritol, or an alkoxylated, preferably ethoxylated or propoxylated) derivative thereof. It will be appreciated that it is also possible to use mixtures of a plurality of different trifunctional alcohols. Preferred trifunctional alcohols are glycerol, trimethylolpropane and pentaerythritol. Very particular preference is given to glycerol and trimethylolpropane.

Alkoxylated derivatives of glycerol, trimethylolethane, trimethylolpropane, bis(trimethylolpropane), pentaerythritol can be obtained in a manner known in principle by alkoxylating the alcohols with alkylene oxide, such as ethylene oxide, propylene oxide, butylene oxide, and/or pentylene oxide. The mixed alkoxylated polyetherols may be copolymers in which, for example, different alkylene oxide units are distributed randomly in the chain, or they may be block copolymers.

The alkoxylated derivative of glycerol, trimethylolethane, trimethylolpropane, bis(trimethylolpropane) or pentaerythritol is preferably alkoxylated with 1.1 to 20 alkylene oxide units, preferably ethylene oxide and/or propylene oxide units. The alkoxylated derivative of glycerol, trimethylolpropane or pentaerythritol is most preferably alkoxylated with 1.1 to 20 propylene oxide units.

In addition to the components mentioned, it is optionally also possible to use further components to synthesize the hyperbranched polymers used in accordance with the invention. Such components can be used to influence the properties of the polymers and adjust them optimally for the desired purpose.

For instance, it is possible to use further di- or polyfunctional carboxylic acids. Examples of further carboxylic acids comprise malonic acid, succinic acid, glutaric acid, adipic acid, 1,2-, 1,3- or 1,4-cyclohexanedicarboxylic acid (hexahydrophthalic acids), phthalic acid, isophthalic acid, terephthalic acid or derivatives thereof, especially the anhydrides or esters thereof. The amount of such further carboxylic acids should, however, generally not exceed 50 mol % based on the amount of all carboxylic acids used (i.e. sum of hydrophobic dicarboxylic acids and further di- or polyfunctional carboxylic acids) together.

In addition, as well as the trifunctional alcohols, it is also possible to use difunctional aliphatic, cycloaliphatic, aralipahtic or aromatic diols. The suitable selection of dihydric alcohols can influence the properties of the polyesters. Examples of suitable diols are ethylene glycol, 1,2-propanediol, 1,3-propanediol, 1,4-butanediol, 1,5-pentanediol, 1,6-hexanediol, 1,8-octanediol, 1,2-, 1,3- and 1,4-cyclohexanediol, 1,3- and 1,4-bis(hydroxymethyl)cyclohexane, and also diethylene glycol, triethylene glycol, dipropylene glycol, tripropylene glycol, polyethylene glycols $HO(CH_2CH_2O)_n$—H or polypropylene glycols $HO(CH[CH_3]CH_2O)_n$—H, where n is an integer and n is 4, polyethylene-polypropylene glycols, where the sequence of the ethylene oxide or propylene oxide units may be blockwise or random, or polytetramethylene glycols, preferably up to a molar mass of 5000 g/mol. The dihydric alcohols may optionally also comprise further functionalities, for example carbonyl, carboxyl, alkoxycarbonyl or sulfonyl functions, for example dimethylolpropionic acid or dimethylolbutyric acid, and the $C_1$-$C_4$-alkyl esters thereof, glyceryl monostearate or glyceryl monooleate. The amount of such further dihydric alcohols should, however, generally not exceed 50 mol % based on the amount of all alcohols used (i.e. sum of trifunctional alcohol and difunctional diol). The amount of dihydric alcohols is preferably not more than 30 mol %, more preferably not more than 20 mol %. Most preferably, only the trifunctional alcohols are used.

The conversion of all components of the hyperbranched polyester can be performed in the presence or absence of a solvent. Suitable solvents are, for example, hydrocarbons such as paraffins, aromatics, ethers and ketones. Preferably, the reaction is, however, performed free of solvent.

The reaction is effected generally at elevated temperatures, for example 30 to 250° C., especially 80 to 220° C. and more preferably 80 to 180° C.

The water or the alcohols formed during the polymerization (polycondensation) should be removed from the reaction medium by means of suitable measures. The reaction can be effected, for example, in the presence of a water-withdrawing agent as an additive which is added at the start of the reaction. Suitable examples are molecular sieves, especially 4 Å molecular sieve, anhydrous $MgSO_4$ or anhydrous $Na_2SO_4$. In addition, water or alcohols formed during the reaction can be distilled off. This can also be done by means of a suitable entraining agent using a water separator. The distillation can preferably be effected under reduced pressure, for example at a pressure of 1 mbar to 500 mbar.

The reaction can be performed in the absence of catalysts. Preference is given, however, to working in the presence of at least one catalyst. The catalysts are preferably acidic inorganic, organometallic or organic catalysts, or mixtures of a plurality of acidic inorganic, organometallic or organic catalysts. It is also possible to use enzymes as catalysts, although the use thereof is less preferred.

Acidic inorganic catalysts for the purposes of the present invention are for example sulfuric acid, sulfates and hydrogen sulfates, such as sodium hydrogen sulfate, phosphoric acid, phosphonic acid, hypophosphorous acid, aluminum sulfate hydrate, alum, acidic silica gel (pH≤6, especially ≤5) and acidic aluminum oxide. Further acidic inorganic catalysts which can be used include, for example, aluminum compounds of the general formula $Al(OR^1)_3$ and titanates of the general formula $Ti(OR^1)_4$, it being possible for the radicals $R^1$ to be identical or different in each case and to be selected independently of one another from $C_1$-$C_{20}$ alkyl radicals, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, 2-ethylhexyl, n-nonyl, n-decyl, n-dodecyl, n-hexadecyl or n-octadecyl, for example; $C_3$-$C_{12}$ cycloalkyl radicals, such as cyclopropyl, cyclobutyl, cyclopentyl, cyclohexyl, cycloheptyl, cyclooctyl, cyclononyl, cyclodecyl, cycloundecyl and cyclododecyl, for example; preferably cyclopentyl, cyclohexyl and cycloheptyl. The radicals $R^1$ in $Al(OR^1)_3$ and/or $Ti(OR^1)_4$ are preferably each identical and selected from n-butyl, isopropyl and 2-ethylhexyl.

Preferred acidic organometallic catalysts are chosen for example from dialkyltin oxides $R^1{}_2SnO$ or dialkyltin diesters $R^1{}_2Sn(OR^2)_2$ in which $R^1$ is as defined above and can be identical or different. $R^2$ can have the same definitions as $R^1$ and additionally can be $C_6$-$C_{12}$ aryl: phenyl, o-, m- or p-tolyl, xylyl or naphthyl, for example. $R^2$ can in each case be identical or different. Examples of organotin catalysts are tin(II) n-octanoate, tin(II) 2-ethylhexanoate, tin(II) laurate, dibutyltin oxide, diphenyltin oxide, dibutyltin dichloride, dibutyltin diacetate, dibutyltin dilaurate, dibutyltin dimaleate or dioctyltin diacetate. Also conceivable are organoantimony, -bismuth or -aluminum catalysts. Particularly preferred representatives of acidic organometallic catalysts are dibutyltin oxide, diphenyltin oxide and dibutyltin dilaurate.

Preferred acidic organic catalysts are acidic organic compounds containing, for example, phosphate groups, sulfonic acid groups, sulfate groups or phosphonic acid groups. Particular preference is given to sulfonic acids such as para-toluenesulfonic acid, for example. Acidic ion exchangers can also be used as acidic organic catalysts, examples being polystyrene resins which contain sulfonic acid groups and have been crosslinked with about 2 mol % of divinylbenzene.

Combinations of two or more of the aforementioned catalysts can also be employed. A further possibility is to use organic or organometallic or else inorganic catalysts that are in the form of discrete molecules in an immobilized form, on silica gel or on zeolites, for example. If it is desired to use acidic inorganic, organometallic or organic catalysts then the amount of catalyst used is in accordance with the invention from 0.001% to 10% by weight, preferably from 0.01% to 1% by weight.

The reaction time is typically from 5 minutes to 48 hours, preferably from 30 minutes to 24 hours and more preferably from 1 hour to 10 hours. The end of the reaction can often be recognized by the fact that the viscosity of the reaction mixture suddenly starts to rise rapidly. When the viscosity rise begins, the reaction can be stopped, for example by cooling. Thereafter, the carboxyl group number in the (pre) polymer can be determined on a sample of the mixture, for example by titration of the acid number to DIN 53402-2.

The reaction of the monomers described typically forms ester bonds. The resulting hyperbranched polyesters are essentially uncrosslinked. In the context of this invention, essentially uncrosslinked means that a degree of crosslinking of less than 15% by weight, preferably of less than 10% by weight, determined via the insoluble content of the polymer, is present. The insoluble content of the polymer was determined by extraction for four hours with the same solvent as is used for the gel permeation chromatography, i.e. tetrahydrofuran, dimethylacetamide or hexafluoroisopropanol, according to the solvent in which the polymer has better solubility, in a Soxhlet apparatus and, after drying the residue to constant weight, weighing the remaining residue.

When working without solvent, the end product is generally obtained directly and, if required, can be purified by customary purifying operations. When a solvent has also been used, it can typically be removed from the reaction mixture after the reaction, for instance by vacuum distillation.

The preparation is notable for its great simplicity. It enables the preparation of hyperbranched polyesters in a simple one-pot reaction. The isolation or purification of intermediates or protecting groups for intermediates is not required. Further details of the preparation of hyperbranched polyesters are given, for example, in WO 01/46296, DE 101 63 163, DE 102 19 508, DE 102 40 817 or WO 99/16810. The hyperbranched polyesters are prepared usually within a pressure range from 2 mbar to 20 bar, preferably at standard pressure, in reactors or reactor cascades which are operated batchwise, semicontinuously or continuously. Through the aforementioned establishment of the reaction conditions and optionally through the selection of the suitable solvent, the inventive products can be processed further without further purification after the preparation.

Preference is given to hyperbranched polyesters which have a weight-average molecular weight in the range from about 500 to 100 000, more preferably of 1000 to 50 000. In the case of a hyperbranched polyester joined to one polyalkylene oxide group, the molecular weight relates only to the part of the hyperbranched polyester without the polyalkylene oxide group. The determination is usually effected by gel permeation chromatography with a refractometer as the detector. Preference is given to performing the determination as described in the examples.

The polydispersity of the polyesters used in accordance with the invention is generally from 1.2 to 50, preferably from 1.4 to 40, more preferably from 1.5 to 30 and most preferably from 2 to 30. The polydispersity data and the number-average and weight-average molecular weight data $M_n$ and $M_w$ are based here on gel permeation chromatography analyses, using polymethyl methacrylate as the standard and tetrahydrofuran, dimethylacetamide or hexafluoroisopropanol as the eluent. The method is described in Analytiker Taschenbuch [Analyst's Handbook], Volume 4, pages 433 to 442, Berlin 1984.

The type of terminal groups can be influenced by the ratio of the monomers used. If predominantly OH-terminated polymers are to be obtained, the alcohols should be used in excess. If predominantly COOH-terminated polymers are to be obtained, the carboxylic acids should be used in excess.

The number of free OH groups (hydroxyl number) of the hyperbranched polyester is generally from 10 to 500 mg, preferably from 20 to 450 mg of KOH per gram of polymer and can be determined, for example, by titration to DIN 53240-2.

The number of free COOH groups (acid number) of the hyperbranched polyester is generally from 0 to 400, preferably from 25 to 300, even more preferably 50 to 250 and especially 120 to 250 mg KOH per gram of polymer and can likewise be determined by titration to DIN 53402.

The hyperbranched polyesters used in accordance with the invention generally have at least 4 functional groups. There is in principle no upper limit in the number of functional groups. However, products having too high a number of functional groups frequently have undesired properties, for example poor solubility or a very high viscosity. The hyperbranched polymers used in accordance with the invention therefore generally have not more than 100 functional groups. The hyperbranched polymers preferably have from 6 to 50 and more preferably from 6 to 30 functional groups.

The hyperbranched polyester is preferably joined to a polar polymer which comprises a polycondensate or a polymer comprising ethylenically unsaturated monomers.

The hyperbranched polyester is preferably joined to the polar polymer by means of a polyisocyanate linker. The linker-reactive group used may be a hydroxyl group at the chain end of the polar polymer. Preference is given to polar polymers which have exactly one linker-reactive group at the chain end. Suitable polyisocyanate linkers are polyisocyanates with a functionality based on the isocyanate groups of at least 1.5, particularly 1.5 to 4.5 and especially 1.8 to 3.5, comprising aliphatic, cycloaliphatic and aromatic di- and polyisocyanates, and the isocyanurates, allophanates, uretdiones and biurets of aliphatic, cycloaliphatic and aromatic diisocyanates. The polyisocyanates preferably have an average of 1.8 to 3.5 isocyanate groups per molecule. Examples of suitable polyisocyanates are aromatic diisocyanates such as toluene 2,4-diisocyanate, toluene 2,6-diisocyanate, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate, and cycloaliphatic diisocyanates such as isophorone diisocyanate (IPDI), cyclohexylene 1,2-diisocyanate, cyclohexylene 1,4-diisocyanate and bis(4,4'-isocyanatocyclohexyl)methane. Among the polyisocyanates, preference is given to those whose isocyanate groups differ in terms of reactivity, such as toluene 2,4-diisocyanate, toluene 2,6-diisocyanate, 4'-diphenylmethane diisocyanate, cis- and trans-isophorone diisocyanate, or mixtures of these compounds.

The reaction with the polyisocyanate linker is effected in the melt or in an organic solvent, preferably in an aprotic polar organic solvent or mixtures of such solvents. Examples are ketones (for example acetone), butyl acetate, tetrahydrofuran (THF), xylene, chlorobenzene, dimethyl sulfoxide (DMSO) or dimethylformamide (DMF). Preferred solvents are butyl acetate, xylene and acetone. The reaction is effected typically at elevated temperatures, the temperature also being guided by the boiling temperature of the solvent selected. The reaction of the polyisocyanate linker with the first component can be effected at 20 to 80° C., but if desired also up to 100° C. The reaction of the further isocyanate group can be effected at temperatures of 50 to 100° C. The solvent can subsequently be removed by distillation.

The reaction can be effected in an equimolar manner, which means that the quantitative ratio is selected such that 1 mol of diisocyanate is used per mole of hydroxyl groups of the functionalizing reagent or of the linear polyalkylene oxide to be converted. Preference is given to working with a slight (e.g. 0 to 15 mol %) excess of the hydroxyl groups, in order to reduce the amount of unconverted diisocyanate. In the case of symmetric diisocyanates (such as HDI), it may also be advisable to use an excess of diisocyanate and to remove the excess subsequently by distillation.

Preference is given to performing the reaction in the presence of a catalyst. Suitable catalysts are, for example, tertiary amines, for example triethylamine, tri-n-propylamine, N-methylpyrrolidine, N-methylpiperidine and diazabicyclooctane (DABCO), zinc carboxylates, bismuth carboxylates, titanium alkoxides, organotin compounds, especially dialkyltin(IV) salts of aliphatic carboxylic acids such as dibutyltin dilaurate and dibutyltin dioctoate, tin(II) dialkoxides such as tin dioctoate, and cesium salts such as cesium acetate. In one embodiment, tin carboxylates, bismuth carboxylates, titanium alkoxides are particular suitable, the carboxylates preferably being $C_1$-$C_{20}$ carboxylates (such as formate, acetate, propionate, hexanoate, octanoate or neodecanoate). The catalyst can be used in amounts of 50 to 50 000 ppm, preferably 100 to 5000 ppm, based on all of the solids.

Typically, the reaction will be performed in such a way that the component which is to be functionalized with isocyanate groups (for example the polar polymer) is first reacted with the diisocyanate in the presence of the catalyst and of a solvent until the isocyanate value in the reaction mixture has fallen by half. When a slight hydroxyl group excess is used, conversion is continued until the theoretical end value corresponds to the complete conversion of the hydroxyl groups. This can be determined in a known manner, for example by titrimetric means. This is then followed by the addition of the hyperbranched polyester. The molar ratio of hyperbranched polyester to the polyalkylene oxide or to the functional $C_1$-$C_{24}$ end group comprising one acid group or two alcohol groups is 1:1 to 1:25, preferably 1:2 to 1:15. The reaction is continued until the isocyanate value has fallen to zero.

The polycondensate is preferably a block polymer comprising a) a polyester or polyurethane block, and b) a polyethylene glycol block.

Suitable polyethylene glycols for a block are polyethylene glycol or polyethylene glycol monoalkyl ether having a molar mass Mn of 200 to 10 000 g/mol.

Suitable polyesters for a block are those based on hydroxycarboxylic acid compounds, dialcohol compounds or diacid compounds, particularly hydroxycarboxylic acid compounds. Preferred hydroxycarboxylic acid compounds are lactones, especially $C_4$ to $C_{18}$-alkyl lactones, most preferably ε-caprolactone.

Suitable polyurethanes for a block are based on at least one diisocyanate and at least one diol. Suitable diisocyanates are compounds with at least two isocyanate groups. Useful diisocyanates include all aliphatic, cycloaliphatic, araliphatic and aromatic di- or polyisocyanates which are known in the prior art and mentioned by way of example hereinafter. Mention should be made here preferably of 4,4'-diphenylmethane diisocyanate, the mixtures of monomeric diphenylmethane diisocyanates and oligomeric diphenylmethane diisocyanates (polymer MDI), tetramethylene diisocyanate, tetramethylene diisocyanate trimers, hexamethylene diisocyanate, hexamethylene diisocyanate trimers, isophorone diisocyanate trimer, 4, 4'-methylenebis(cyclohexyl)diisocyanate, xylylene diisocyanate, tetramethylxylylene diisocyanate, dodecyl diisocyanate, lysine alkyl ester diisocyanate, where alkyl represents C1 to C10, 1,4-diisocyanatocyclohexane or 4-isocyanatomethyl-1,8-octamethylene diisocyanate. The diols used may be branched or linear alkanes having 2 to 18 carbon atoms, preferably 4 to 14 carbon atoms, cycloalkanes having 5 to 20 carbon atoms or aromatic compounds, which comprise at least two alcohol groups, and mixtures of these diols. Preference is given to branched or linear alkanes, such as ethylene glycol, 1,2-propanediol, 1,3-propanediol, 1,2-butanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 2,4-dimethyl-2-ethyl-1,3-hexanediol, 2,2-dimethyl-1,3-propanediol (neopentyl glycol), 2-ethyl-2-butyl-1,3-propanediol, 2-ethyl-2-isobutyl-1,3-propanediol or 2,2,4-trimethyl-1,6-hexanediol. Especially suitable are ethylene glycol, 1,3-propanediol, 1,4-butanediol and 2,2-dimethyl-1,3-propanediol, 1,6-hexanediol or 1,12-dodecanediol.

The polymer comprising ethylenically unsaturated monomers is preferably a random copolymer or a block polymer. The polymer is more preferably a random copolymer, comprises polyethylene glycol monomethyl ether (meth)acrylate or allyl alcohol alkoxylate in polymerized form, or a block polymer comprising a block based on a polar, ethylenically unsaturated monomer.

Examples of random copolymers are random copolymers of polar, ethylenically unsaturated monomers, preferably of vinylpyrrolidone, (meth)acrylic acid, polyethylene glycol monomethyl ether (meth)acrylate, polyethylene glycol (meth)acrylate, or allyl alcohol alkoxylate, especially of polyethylene glycol monomethyl ether (meth)acrylate or allyl alcohol alkoxylate. As further monomers, the random copolymer may comprise: esters of acrylic acid with $C_1$-$C_{10}$-alkanols, such as ethyl acrylate, n-butyl acrylate, isobutyl acrylate, tert-butyl acrylate, n-hexyl acrylate, 2-ethylhexyl acrylate and 3-propylheptyl acrylate, the esters of methacrylic acid with $C_1$-$C_{10}$-alkanols, such as methyl methacrylate, ethyl methacrylate, n-butyl methacrylate, isobutyl methacrylate, tert-butyl methacrylate and n-hexyl methacrylate, N—($C_2$-$C_{10}$-alkyl)amides of acrylic acid and of methacrylic acid, and the N—($C_1$-$C_2$-alkyl)-N—($C_2$-$C_{10}$-alkyl) amides of acrylic acid and of methacrylic acid, e.g. N-ethylacrylamide, N,N-diethylacrylamide, N-butylacrylamide, N-methyl-N-propylacrylamide, N-(n-hexyl)acrylamide, N-(n-octyl)-acrylamide and the corresponding methacrylamides, vinylaromatic monomers such as styrene, methylstyrene, vinyltoluene, olefins having 2 to 10 carbon atoms, preferably α-olefins having 3 to 10 carbon atoms, such as propene, 1-butene, 1-pentene, 1-hexene, 1-octene and 1-decene, vinyl esters of aliphatic carboxylic acids, such as vinyl acetate, vinyl propionate, vinyl laurate, vinyl nonanoate, vinyl decanoate, vinyl laurate and vinyl stearate, unsaturated nitriles such as acrylonitrile and methacrylonitrile, halogenated olefins such as vinyl chloride, $C_{11}$-$C_{20}$-alkyl esters of monoethylenically unsaturated monocarboxylic acids having preferably 3 to 6 carbon atoms, e.g. $C_{11}$-$C_{20}$-alkyl acrylates and $C_{11}$-$C_{20}$-alkyl methacrylates, such as lauryl acrylate, lauryl methacrylate, isotridecyl acrylate, isotridecyl methacrylate, stearyl acrylate, stearyl methacrylate, di-$C_1$-$C_{20}$-alkyl esters of ethylenically unsaturated dicarboxylic acids having preferably 4 to 8 carbon atoms, e.g. di-$C_1$-$C_{20}$-alkyl esters of fumaric acid and of maleic acid, such as dimethyl fumarate, dimethyl maleate, dibutyl fumarate and dibutyl maleate, glycidyl esters of monoethylenically unsaturated monocarboxylic acids having preferably 3 to 6 carbon atoms, such as glycidyl acrylate and glycidyl methacrylate. Preferred further monomers are the esters with $C_1$-$C_{10}$-alkanols of acrylic acid and of methacrylic acid.

The polymer comprising ethylenically unsaturated monomers is, in a preferred embodiment, a block polymer comprising a block of at least one polar, ethylenically unsaturated monomer. The molar mass Mn is usually in the range of 200-10 000 g/mol, preferably between 300 and 2000 g/mol, and can be determined by GPC. The block polymer may be of the A-B or A-B-A type, preferably of the A-B type. The preparation of block polymers of these types is common knowledge. Suitable and preferred polar, ethylenically unsaturated monomers are vinylpyrrolidone, (meth)acrylic acid, sulfo-containing ethylenically unsaturated monomers, amino-functional, ethylenically unsaturated monomers, or a (meth)acrylic ester of a polyethylene glycol derivative.

Examples of a block of at least one polar, ethylenically unsaturated monomer are polyvinylpyrrolidone or poly (meth)acrylic acid or polyethylene glycol monomethyl ether (meth)acrylate. The other block in each case can be formed from prior art polymer blocks. The other block is preferably nonpolar, for example is formed from caprolactone or propylene oxide. In a further embodiment, the other block comprises polyester (for example based on a dicarboxylic acid and a diol), polyamide (for example based on a dicarboxylic acid and a diamine), polycarbonate, polyurethane or polyurea. Preferred block polymers are polyethylene glycol-block-polycaprolactone and polyethylene glycol monomethyl ether-block-polycaprolactone and polypropylene glycol-block-polyethylene glycol.

The inventive composition is obtainable by contacting the hyperbranched polyester and the active ingredient which has a maximum solubility in water at 20° C. of 10 WI. The components can be contacted by commonly known methods, such as mixing, emulsifying or suspending.

The weight ratio of hyperbranched polyester to active ingredient is usually in the range from 1:50 to 100:1, preferably 1:5 to 50:1, more preferably 1:2 to 25:1. The active ingredient may be present in dissolved form or in solid particulate form. The active ingredient particles may be crystalline or amorphous. The particle size may be 1 nm to 10 μm.

The composition may be in the form of a solid, solution, emulsion, suspension or suspoemulsion of the active ingredient. The inventive composition is preferably an aqueous composition. In a further preferred embodiment, the inventive composition is a solid, and is more preferably a solid solution. In the case of solid solutions, the active ingredient is typically in amorphous form, dispersed in a polymer matrix. It preferably comprises at least 40% by weight, more preferably at least 60% by weight and especially at least 80% by weight of water. The composition typically comprises at most 99% by weight of water.

The inventive composition may comprise formulating assistants, the selection of the assistants typically being guided by the specific application form and the active ingredient. Examples of suitable formulating assistants are solvents, solid carriers, surfactants (including protective colloids, wetters and stickers), organic and inorganic thickeners, bactericides, antifreezes, defoamers, and optionally dyes and adhesives (for example for seed treatment).

Useful surfactants (adjuvants, wetters, stickers, dispersants or emulsifiers) include the alkali metal, alkaline earth metal, ammonium salts of aromatic sulfonic acids, for example of lignosulfonic acid (Borresperse® products, Borregaard, Norway), phenolsulfonic acid, naphthalenesulfonic acid, (Morwet® products, Akzo Nobel, USA) and dibutylnaphthalenesulfonic acid (Nekal® products, BASF, Germany), and also of fatty acids, alkyl- and alkylarylsulfonates, alkyl ether, lauryl ether and fatty alcohol sulfates, and salts of sulfated hexa-, hepta- and octadecanols, and of fatty alcohol glycol ethers, condensation products of sulfonated naphthalene and derivatives thereof with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

In a preferred embodiment, the active ingredient is a pesticide and the inventive compositions are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition is preferably in the form an emulsifiable concentrate (EC), of a suspension concentrate (SC), of a water-soluble concentrate (SL), of a solution for seed treatment (LS), or of a redispersible concentrate (DC).

The agrochemical formulation is usually diluted before use in order to produce the so-called tankmix. Useful substances for dilution include mineral oil fractions of moderate to high boiling point, such as kerosene or diesel oil, and also coal tar oils and oils of vegetable or animal origin, aliphatic, cyclic and aromatic hydrocarbons, for example toluene, xylene, paraffin, tetrahydronaphthalene, alkylated naphthalenes or derivatives thereof, methanol, ethanol, propanol, butanol, cyclohexanol, cyclohexanone, isophorone, highly polar solvents, for example dimethyl sulfoxide, N-methylpyrrolidone or water. Preference is given to using water. It is also possible not to add the amphiphile until the tankmix stage. In this embodiment, the inventive composition is present in the form of a tankmix.

The diluted composition is typically applied by spraying or nebulizing. Immediately before application (tankmix), it is possible to add to the tankmix oils of various types, wetters, adjuvants, herbicides, bactericides, fungicides. These agents can be added to the inventive compositions in a weight ratio of 1:100 to 100:1, preferably 1:10 to 10:1. The pesticide concentration in the tankmix can be varied within relatively wide ranges. In general, it is between 0.0001 and 10%, preferably between 0.01 and 1%. The application rates in the case of application in crop protection, according to the type of effect desired, are between 0.01 and 2.0 kg of active ingredient per ha.

The use of the agrochemical formulations is possible for control of phytopathogenic fungi and/or undesired plant growth and/or undesired insect or mite infestation and/or for regulation of the growth of plants, by allowing the composition to act on the particular pests, the habitat thereof or the plants to be protected from the particular pest, the soil and/or undesired plants and/or the crop plants and/or the habitat thereof. In addition, it is possible to use the agrochemical formulations to control undesired insect or mite infestation on plants and/or to control phytopathogenic fungi and/or to control undesired plant growth, by treating seeds of crop plants with the composition.

The invention also relates to a hyperbranched polyester which is joined to a polar polymer which comprises a polycondensate or a polymer comprising ethylenically unsaturated monomers. Suitable and preferred embodiments of the hyperbranched polyester and of the polar polymer are as described above.

The invention further relates to a process for preparing the inventive hyperbranched polyester, by reacting the polyester, the polar polymer and a linker. Suitable and preferred embodiments of the process are as described above.

The invention further relates to use of the inventive hyperbranched polyester for solubilizing an active ingredient which has a maximum solubility in water at 20° C. of 10 g/l in aqueous solutions. "Solubilization" means that more active ingredient can be brought into solution in the presence of the hyperbranched polyester than in the absence thereof under otherwise identical conditions. It is preferably possible to bring at least twice the amount, more preferably at least five times the amount and especially ten times the amount into solution.

Advantages of the present invention are that a high concentration of active ingredient can be brought into solution; that the preparation of the hyperbranched polyester is possible in a very simple manner and on the industrial scale; and that the amphiphile itself is water-soluble or water-dispersible. A further advantage of the invention is that the hyperbranched polyesters are particularly hydrolysis-stable as a result of use of the hydrophobic dicarboxylic acid and/or as a result of use of stable linker molecules which form, for example, urethane bonds. As a result of this, the inventive polyesters can be used particularly efficiently to produce storage-stable agrochemical formulations.

Further advantages are that the bioavailability of the active ingredients is increased, that the systemic effect of the active agrochemical ingredients in the case of foliar uptake is increased, that even sparingly soluble active agrochemical ingredients can now be formulated in dissolved form, for example, as SL (water-soluble concentrate) or LS (solution for seed treatment), that the distribution of the active agrochemical ingredients in the spray solution is improved, and that the reusable packaging of the active ingredients and the application devices (e.g. the spray devices for pesticides) can be cleaned more efficiently with water.

The examples which follow illustrate the invention without restricting it.

EXAMPLES

DBTL: dibutyltin dilaurate

PEGMEMA 475: polyethylene glycol monomethyl ether methacrylate (M=475 g/mol)

PEGMEMA 1100: polyethylene glycol monomethyl ether methacrylate (M=1100 g/mol)

AIBN: azobis(isobutyronitrile)

Zinc neodecanoate: available commercially as Tegokat 616, TIB Chemicals.

TMP×15.7 PO: reaction product of trimethylolpropane with 15.7 molar excess of propylene oxide.

ASA 12: commercially available alkenylsuccinic anhydrides (Trigon Chemie), the alkenyl radicals being unsaturated $C_{12}$ units.

The hyperbranched polymers were analyzed by gel permeation chromatography, using a refractometer as detector. The mobile phase used was THF, while the standard used for determining the molecular weight was polymethyl methacrylate (PMMA). The acid number was determined in each case in accordance with DIN 53402. The OH number was determined (mg KOH/g) in a method based on DIN 53240, Part 2. The amine number was determined by titration with hydrochloric acid, using a pH indicator. The molar masses of the linear-dendritic copolymers were determined arithmetically from the number-average molecular weight of the parent hyperbranched core, its amine number, and the selected degree of functionalization (stoichiometric ratio of NCO groups of the functional linear polymers/available amine groups of the core molecule) (assuming a quantitative addition reaction of the linker-reactive groups to the linker).

Example 1

Preparation of a Linear-Dendritic Copolymer Based on a Hydrophobic Hyperbranched Polyester Core (A.1a) and a Shell of a Comblike PMMA-co-PS-co-PEGMEMA Copolymer, Degree of Functionalization 40%, A.1

Stage 1: Hyperbranched polyester with terminal OH groups, A.1a

With dry nitrogen gassing, 200.0 g of the trifunctional alcohol trimethylolpropane (TMP) and 300.7 g of sebacic acid were introduced, 0.09 g of DBTL catalyst was added, and the reaction mixture was heated to 160-190° C. with stirring. After a reaction time of 105 minutes and the deposition of a quantity of water of 39 ml (conversion 72%), the reaction was ended by cooling to room temperature. The polymer A.1a (Mn=1400 g/mol; Mw=34 500 g/mol; OH number: 210 mg KOH/g polymer; acid number: 40 mg KOH/g polymer) was obtained in the form of a yellow-colored liquid of high viscosity which was not water-soluble.

Stage 2 (A.1b): 250.0 g of tetrahydrofuran (THF) were introduced under nitrogen and then heated under reflux. Over the course of 2 hours, a mixture 1 of 180.2 g of methyl methacrylate, 70.3 g of styrene, and 214.0 g of PEGMEMA 475 and also, at the same time, over the course of 4 hours, a mixture 2 of 8.6 g of AIBN and 27.0 g of mercaptoethanol, in solution in 250.0 g of THF, were added slowly to the batch by means of two metering pumps. After the end of addition of mixture 2, the reaction mixture was heated under reflux for a further 16 hours. Subsequent monitoring for residual monomers by means of GC indicated an MMA fraction of <1%, and so the batch was cooled and the product A.1b (Mn=1030 g/mol) was used further directly in stage 3.

Stage 3 (A.1c): 250.0 g of the reaction mixture A.1b were introduced and freed from the THF solvent under reduced pressure. After cooling to room temperature, the batch was placed under nitrogen and the residue was dissolved in 126.5 g of butyl acetate. Then 17.45 g of isophorone diisocyanate (IPDI) were added and the mixture was heated to 50° C. Reaction was commenced by addition of 30 mg of zinc neodecanoate in solution in 1 ml of butyl acetate, and was continued over the course of about 5 hours at 50° C. until the NCO content was 1.07%. The reaction was subsequently ended by cooling to −20° C. The reaction product A.1c was used directly in stage 4 without further workup.

Stage 4 (A.1): 19.0 g of the hydrophobic hyperbranched polyester core A.1a were introduced and dissolved under nitrogen in 13.0 g of butyl acetate. The batch was then admixed with 119.2 g of the reaction mixture A.1c, after which it was heated to 80° C. and the reaction was commenced by addition of 80 mg of DBTL in solution in 1 ml of butyl acetate. Following the complete conversion of all the NCO groups (NCO content 0%), the batch was cooled and the solvent was removed under reduced pressure. Finally the linear-dendritic copolymer A.1 (Mn=4000 g/mol) was obtained in the form of a yellow-colored liquid of high viscosity which was fully water-soluble.

Example 2

Preparation of a Linear-Dendritic Copolymer Based on a Hydrophobic Hyperbranched Polyester Core (A.1a) and a Shell of a Comblike PVP-co-Plauryl Acrylate-co-PEGMEMA Copolymer, Degree of Functionalization 100%, A.2

Stage 1: Hyperbranched polyester with terminal OH groups, A.1a

See example 1, stage 1.

Stage 2 (A.2b): 100.0 g of tetrahydrofuran (THF) were introduced under nitrogen and then heated under reflux. Over the course of 3 hours, a mixture 1 of 155.9 g of lauryl acrylate, 144.2 g of N-vinylpyrrolidone and 163.3 g of PEGMEMA 475, in solution in 200.0 g of THF, and also, at the same time, over the course of 4 hours, a mixture 2 of 8.8 g of AIBN and 27.8 g of mercaptoethanol, in solution in 200.0 g of THF, were added slowly to the batch by means of two metering pumps. After the end of addition of mixture 2, the reaction mixture was heated under reflux for a further 18 hours. Subsequent monitoring for residual monomers by means of GC indicated a fraction of lauryl acrylate of <1%, and so the batch was cooled and the product A.2b (Mn=1000 g/mol) was used further directly in stage 3.

Stage 3 (A.2c): 278.4 g of the reaction mixture A.2b were introduced and freed from the THF solvent under reduced pressure. After cooling to room temperature, the batch was placed under nitrogen and the residue was dissolved in 140.0 g of butyl acetate. Then 20.0 g of IPDI were added and the mixture was heated to 50° C. Reaction was commenced by addition of 21 mg of zinc neodecanoate in solution in 1 ml of butyl acetate, and was continued over the course of about 6 hours at 60° C. and also in total about 16 hours at room temperature until the NCO content was 1.16%. The reaction was subsequently ended by cooling to −20° C. The reaction product A.2c was used directly in stage 4 without further workup.

Stage 4 (A.2): 1.0 g of the hydrophobic hyperbranched polyester core A.1a were introduced and dissolved under nitrogen in 1 g of butyl acetate. The batch was then admixed with 15.7 g of the reaction mixture A.2c, after which it was heated to 80° C. and the reaction was commenced by heating to 80° C. Following the complete conversion of all the NCO groups (NCO content 0%), the batch was cooled and the solvent was removed under reduced pressure. Finally the linear-dendritic copolymer A.2 (Mn=7750 g/mol) was obtained in the form of a yellow-colored liquid of high viscosity which was fully water-soluble.

Example 3

Preparation of a Linear-Dendritic Copolymer Based on a Hydrophobic Hyperbranched Polyester Core (A.3a) and a Shell of a Comblike PVP-co-Plauryl Acrylate-co-PEGMEMA Copolymer, Degree of Functionalization 100%, A.3

Stage 1: Hyperbranched polyester with terminal OH groups, A.3a

With dry nitrogen gassing, 432.0 g of the trifunctional alcohol TMP×15.7 PO and 168.0 g of sebacic acid were introduced, 0.1 g of DBTL catalyst was added, and the reaction mixture was heated to 160-180° C. with stirring. After a reaction time of 12 hours and the deposition of a quantity of water of 11.1 ml (conversion 50%), the reaction was ended by cooling to room temperature. The polymer A.3a (Mn=1700 g/mol; Mw=15 000 g/mol; OH number: 73 mg KOH/g polymer; acid number: 67 mg KOH/g polymer) was obtained in the form of a yellow-colored liquid of high viscosity which was not water-soluble.

Stage 2 (A.3b): 100.0 g Tetrahydrofuran (THF) were introduced under nitrogen and then heated under reflux. Over the course of 3 hours, a mixture 1 of 155.9 g of lauryl acrylate, 144.2 g of N-vinylpyrrolidone and 163.3 g of PEGMEMA 475, in solution in 200.0 g of THF, and also, at the same time, over the course of 4 hours, a mixture 2 of 8.8 g of AIBN and 27.8 g of mercaptoethanol, in solution in 200.0 g of THF, were added slowly to the batch by means of two metering pumps. After the end of addition of mixture 2, the reaction mixture was heated under reflux for a further 18 hours. Subsequent monitoring for residual monomers by means of GC indicated a fraction of lauryl acrylate of <1%, and so the batch was cooled and the product A.3b (Mn=1000 g/mol) was used further directly in stage 3.

Stage 3 (A.3c): 278.4 g of the reaction mixture A.3b were introduced and freed from the THF solvent under reduced pressure. After cooling to room temperature, the batch was placed under nitrogen and the residue was dissolved in 140.0 g of butyl acetate. Then 20.0 g of IPDI were added and the mixture was heated to 50° C. Reaction was commenced by addition of 21 mg of zinc neodecanoate in solution in 1 ml of butyl acetate, and was continued over the course of 12 hours at 60° C. and also in total 16 hours at room temperature until the NCO content was 1.14%. The reaction was subsequently ended by cooling to −20° C. The reaction product A.3c was used directly in stage 4 without further workup.

Stage 4 (A.3): 2.0 g of the hydrophobic hyperbranched polyester core A.3a were introduced and dissolved under nitrogen in 2.0 g of butyl acetate. The batch was then admixed with 11.0 g of the reaction mixture A.3c and the reaction was commenced by heating to 80° C. Following the complete conversion of all the NCO groups (NCO content 0%), the batch was cooled and the solvent was removed under reduced pressure. Finally the linear-dendritic copolymer A.3 (Mn=4450 g/mol) was obtained in the form of a yellow-colored liquid of high viscosity which was fully water-soluble.

Example 4

Preparation of a Linear-Dendritic Copolymer Based on a Hydrophobic Hyperbranched Polyester Core (A.1a) and a Shell of a Linear PEG-b-Pcaprolactone Block Copolymer, Degree of Functionalization 100%, A.4

Stage 1: Hyperbranched polyester with terminal OH groups, A.1a

See synthesis example 1, stage 1.

Stage 2 (A.4b): 150.0 g of polyethylene glycol monomethyl ether (Mn=500 g/mol) were introduced and freed from residues of water at 90° C. under reduced pressure. After cooling to room temperature, the batch was placed under nitrogen and the polymer was admixed with 205.0 g of ε-caprolactone. The mixture was heated to 90° C. and the ring-opening polymerization of the caprolactone was commenced by addition of 355 mg of butyltin tris(2-ethylhexanoate). The batch was heated at 90° C. for a further 18 hours and after the end of reaction was cooled to room temperature. The resulting OH-terminated block copolymer A.4b (Mn=1180 g/mol) was used directly in stage 3 without further purification.

Stage 3 (A.4c): 200.0 g of the block copolymer A.4b were introduced, placed under nitrogen, and admixed with 34.1 g of IPDI. The mixture was heated to 50° C. The reaction was commenced by addition of 30 mg of zinc neodecanoate, in solution in 1 ml of butyl acetate, and was run over the course of 4 hours at 50° C. to an NCO content of 2.23%. The reaction was subsequently ended by cooling to −20° C. The reaction product A.4c was used directly in stage 4 without further workup.

Stage 4 (A.4): 1.8 g of the hydrophobic hyperbranched polyester core A.1a were introduced and dissolved under nitrogen in 10.0 g of butyl acetate. The batch was then admixed with 12.6 g of the reaction mixture A.4c, after which it was heated to 80° C. and the reaction was commenced by addition of 14 mg of DBTL in solution in 1 ml of butyl acetate. Following the complete conversion of all the NCO groups (NCO content 0%), the batch was cooled and the solvent was removed under reduced pressure. Finally the linear-dendritic copolymer A.4 (Mn=8690 g/mol) was obtained in the form of a yellow-colored liquid of high viscosity which was fully water-soluble.

Example 5

Preparation of a Linear-Dendritic Copolymer Based on a Hydrophobic Hyperbranched Polyester Core (A.1a) and a Shell of a Linear PEG-b-PUR Block Copolymer, Degree of Functionalization 100%, A.5

Stage 1: Hyperbranched polyester with terminal OH groups, A.1a

See synthesis example 1, stage 1.

Stage 2 (A.5b): 23.4 g of neopentyl glycol and 20.3 g of 1,3-butanediol were dissolved in 100.0 g of THF. The batch was placed under nitrogen and admixed with 100.8 g of hexamethylene diisocyanate (HDI) in solution in 44.5 g of THF. The exothermic reaction was commenced by addition of 140 mg of zinc neodecanoate in solution in 1 ml of THF, and was evident from a rise in temperature to about 50° C. An internal temperature of 50° C. was subsequently maintained by means of an oil bath, and the batch was run, over the course of 7.5 hours at 50° C., to an NCO content of 4.40%. A solution of 300.0 g of polyethylene glycol monomethyl ether (Mn=2000 g/mol) in 300.0 g of THF was subsequently added to the reaction mixture, which was heated at 50° C. for about 4 hours more. When an NCO content of 0.79% was reached, the reaction was ended by cooling to −20° C. The reaction product A.5b (Mn=2960 g/mol) was used directly in stage 3 without further workup.

Stage 3 (A.5): 4.0 g of the hydrophobic hyperbranched polyester core A.1a were introduced and admixed under nitrogen with 76.6 g of the reaction product A.5b, giving a clear solution. The batch was then heated to 50° C. and the reaction was commenced by addition of 4 mg of DBTL in solution in 1 ml of butyl acetate. Following the complete conversion of all the NCO groups (NCO content 0%), the batch was cooled and the solvent THF was removed under reduced pressure. Finally the linear-dendritic copolymer A.5 (Mn=16 790 g/mol) was obtained in the form of a yellow-colored liquid of high viscosity which was fully water-soluble.

Example 6

Preparation of a Linear-Dendritic Copolymer Based on a Hydrophobic Hyperbranched Polyester Core (A.6a) and a Shell of a Comblike PMMA-co-PS-co-PEGMEMA Copolymer, Degree of Functionalization 100%, A.6

Stage 1: Hyperbranched polyester with terminal OH-groups, A.6a

With dry nitrogen gassing, 357.7 g of the trifunctional alcohol TMP×12.2 EO and 142.2 g of alkenylsuccinic anhydride (ASA 12) were introduced, 0.21 g of DBTL catalyst was added, and the reaction mixture was heated to 180-200° C. with stirring. After a reaction time of 23 hours the reaction was ended by cooling to room temperature. The polymer A.6a (Mn=3880 g/mol; Mw=32 560 g/mol; OH number: 94 mg KOH/g polymer; acid number: 9 mg KOH/g polymer) was obtained in the form of a yellow-colored liquid of high viscosity which was not water-soluble.

Stage 2 (A.6b): 250.0 g of THF were introduced under nitrogen and then heated under reflux. Over the course of 2 hours, a mixture 1 of 117.1 g of methyl methacrylate, 44.8 g of styrene, and 315.7 g of PEGMEMA 1100 and also, at the same time, over the course of 4 hours, a mixture 2 of 5.4 g of AIBN and 17.0 g of mercaptoethanol, in solution in 250.0 g of THF, were added slowly to the batch by means of two metering pumps. After the end of addition of mixture 2, the reaction mixture was heated under reflux for a further 20 hours. Subsequent monitoring for residual monomers by means of GC indicated a MMA fraction of <1%, and so the batch was cooled and the product A.6b (Mn=1690 g/mol) was used further directly in stage 3.

Stage 3 (A.6c): 235.0 g of the reaction mixture A.6b were introduced and freed from the THF solvent under reduced pressure. After cooling to room temperature, the batch was placed under nitrogen and the residue was dissolved in 114.5 g of butyl acetate. Then 10.0 g of IPDI were added and the mixture was heated to 50° C. Reaction was commenced by addition of a total of 42 mg of zinc neodecanoate in solution in 1 ml of butyl acetate, and was continued over the course of about 16 hours at 50° C. until the NCO content was 0.76%. The reaction was subsequently ended by cooling to −20° C. The reaction product A.6c was used directly in stage 4 without further workup.

Stage 4 (A.6):

10.0 g of the hydrophobic hyperbranched polyester core A.6a were introduced and dissolved under nitrogen in 10.0 g of butyl acetate. The batch was then admixed with 95.2 g of the reaction mixture A.6c, after which it was heated to 80° C. and the reaction was commenced by addition of 60 mg of DBTL. Following the complete conversion of all the NCO groups (NCO content 0%), the batch was cooled and the solvent was removed under reduced pressure. Finally the linear-dendritic copolymer A.6 (Mn=16 310 g/mol) was obtained in the form of a yellow-colored liquid of high viscosity which was fully water-soluble.

Example 7A

Solubilization of Piroxicam, Carbamazepine, Estradiol and Clotrimazole 2 g of polymer were weighed out into a 50 ml glass beaker. Then 0.2 g of each active ingredient was weighed out into the batch to give a supersaturated solution. Subsequently phosphate buffer at pH 7.0 was added in an amount such as to give a polymer:phosphate buffer mass ratio of 1:9. The mixture was then stirred at room temperature for 72 hours, using a magnetic stirrer. After a rest time of one hour, excess (i.e., unsolubilized) active ingredient was removed by filtration. The resulting clear or opaque solution was then analyzed for its active ingredient content by means of UV spectroscopy or HPLC.

Example 7B

Solubilization of Pyrene, Pyraclostrobin and Fipronil 100 mg of polymer were weighed out into a 50 ml glass beaker and dissolved in 9.900 g of distilled water. Then 100 mg of each active ingredient were weighed out into the batch to give a supersaturated solution. The mixture was then stirred at room temperature for 24 hours, using a magnetic stirrer. After a rest time of one hour, excess (i.e., unsolubilized) active ingredient was removed by centrifuging. The resulting clear or opaque solution was then analyzed for its active ingredient content by means of UV spectroscopy. The wavelengths of the UV-spectroscopic measurement (if applicable) are compiled in table 1.

TABLE 1

| Active ingredient | Wavelength of UV measurement [nm] |
| --- | --- |
| Piroxicam | 356 |
| Carbamazepine | 286 |
| Estradiol | 282 |
| Clotrimazole | HPLC |
| Pyrene | 334 |
| Pyraclostrobin | 277 |
| Fipronil | 280 |

Example 8

Solubilization by Means of Hyperbranched Polyesters

The data were obtained in accordance with the procedures in example 7. The results are compiled in tables 2 and 3.

TABLE 2

| | Solubility of active ingredients [mg/l] with hyperbranched polyester | | | |
| --- | --- | --- | --- | --- |
| Polymer | Piroxicam | Carbamazepine | Estradiol | Clotrimazole |
| none | 420 | 140 | <100 | <100 |
| A.1 | 2150 | 1300 | 1270 | 2510 |
| A.2 | 2880 | 1880 | 1840 | 1910 |

TABLE 3

| | Solubility of active ingredients [mg/l] with hyperbranched polyester | | |
| --- | --- | --- | --- |
| Polymer | Pyrene | Pyraclostrobin | Fipronil |
| none | 0.1 | 22.5 | 3 |
| A.1 | 300 | 1155 | 493 |
| A.2 | 235 | n.d. | 525 |
| A.3 | 291 | n.d. | 615 |

TABLE 3-continued

Solubility of active ingredients [mg/l] with hyperbranched polyester

| Polymer | Pyrene | Pyraclostrobin | Fipronil |
|---|---|---|---|
| A.4 | 290 | n.d. | 547 |
| A.5 | 52 | 258 | n.d. |
| A.6 | 121 | n.d. | 180 | n.d. = not determined

TABLE 4

Solubility of active ingredients [mg/l] with hyperbranched polyester

| Polymer | Pyrene | Fipronil | Solubility in water |
|---|---|---|---|
| A.2 | 235 | 525 | yes |
| A1a (core only) [a] | — | — | no |
| A.2b (shell only) [a] | 171 | 366 | yes |
| Mixture of A.2 and A.1a [a] | — | — | only partial |

[a] not inventive

The direct comparison of A.2 with A.2b shows that the linear-dendritic block copolymer has significantly higher solubilization capacities than the associated shell component on its own.

Example 9

Comparative Tests on Solubilization with Non-Inventive Hyperbranched Polyester

Hyperbranched polyesters based on trimethylolpropane and sebacic acid were compared among one another. The difference lay in the external, polymeric shell, which either consisted of polyethylene glycol (A.12) or was inventive (A.1, A.2, and A.4).

The hyperbranched polyester A.12 was prepared as in European patent application EP 09179828.0 of Dec. 18, 2009 in synthesis example 12. The polymers A.1, A.2, and A.4 have been described above. All of the polymers were tested for their solubilization in accordance with the procedure described above. The results are compiled in table 5. It was shown that here the polymers of the invention exhibit significantly higher solubilization capacities.

TABLE 5

Solubilization with non-inventive hyperbranched polyesters

| Polymer | Core + shell | Pyrene | Pyraclostrobin | Fipronil |
|---|---|---|---|---|
| A.12 [a] | Sebacic acid/TMP + MPEG500 | 180 | 554 | 290 |
| A.1 | Sebacic acid/TMP + P(MMA/S/PEGMA) | 300 | 1155 | 493 |
| A.2 | Sebacic acid/TMP + P(LA/VP/PEGMA) | 235 | n.d. | 525 |
| A.4 | Sebacic acid/TMP + P(PEG-b-PCL) | 290 | n.d. | 547 |

[a] not inventive;
n.d. = not determined. TMP: trimethylolpropane; MPEG500: monomethylpolyethylene glycol, molar mass 500 g/mol.

The invention claimed is:
1. A composition comprising an active ingredient with a maximum solubility in water at 20° C. of 2 g/l and a hyperbranched polyester that is joined to a polar polymer, wherein the polar polymer comprises:
   I) a polycondensate; or
   II) a polymer comprising ethylenically unsaturated monomers;
wherein the hyperbranched polyester is based on:
   III) an aliphatic $C_{10}$-$C_{32}$ dicarboxylic acid, a dicarboxylic acid having a polyisobutylene group, and/or a succinic acid unit having a $C_3$-$C_{40}$ group; and
   IV) glycerol, trimethylolethane, trimethylolpropane, bis(trimethylolpropane), pentaerythritol, or an alkoxylated derivative thereof;
wherein the polycondensate I) is a block polymer comprising:
   a) polyester; and
   b) polyethylene glycol;
wherein the polymer comprising ethylenically unsaturated monomers II) is
   c) a random copolymer comprising polyethylene glycol monomethyl ether (meth)acrylate, or allyl alcohol alkoxylate in polymerized form; and
wherein the polar polymer is connected to the hyperbranched polyester by a polyisocyanate linker.

2. The composition according to claim 1, which comprises at least 10% by weight of water.

3. A hyperbranched polyester joined to a polar polymer, the polar polymer comprising a polycondensate or a polymer comprising ethylenically unsaturated monomers,
wherein the polyester is based on an aliphatic $C_{10}$-$C_{32}$ dicarboxylic acid, a dicarboxylic acid having a polyisobutylene group and/or a succinic acid unit having a $C_3$-$C_{40}$ group;
wherein the polycondensate is a block polymer comprising:
   a) polyester; and
   b) polyethylene glycol;
wherein the polymer comprising ethylenically unsaturated monomers is
   c) a random copolymer comprising polyethylene glycol monomethyl ether (meth)acrylate, or allyl alcohol alkoxylate in polymerized form; and
wherein the polar polymer is connected to the hyperbranched polyester by a polyisocyanate linker.

4. The polyester according to claim 3, wherein the polyester is based on glycerol, trimethylolethane, trimethylolpropane, bis(trimethylolpropane), pentaerythritol, or an alkoxylated derivative thereof.

5. A process for preparing the hyperbranched polyester according to claim 3, comprising reacting the polyester, the polar polymer and a linker.

6. The process of claim 5, wherein the linker is an polyisocyanate.

7. A composition comprising the polyester according to claim 3 and an active ingredient with a maximum solubility in water at 20° C. of 0.5 g/l.

* * * * *